(12) United States Patent
Leon et al.

(10) Patent No.: US 12,001,852 B2
(45) Date of Patent: Jun. 4, 2024

(54) DISTRIBUTED PROCESSING SYSTEM

(71) Applicant: Tyco Fire & Security GmbH, Neuhausen am Rheinfall (CH)

(72) Inventors: Gustavo Leon, Tamarac, FL (US); Stewart E. Hall, Wellington, FL (US); Craig Trivelpiece, Mission Viejo, CA (US); Paul B. Rasband, Fremont, CA (US)

(73) Assignee: Tyco Fire & Security GmbH, Neuhausen am Rheinfall (CH)

( * ) Notice: Subject to any disclaimer, the term of this patent is extended or adjusted under 35 U.S.C. 154(b) by 0 days.

(21) Appl. No.: 16/439,471

(22) Filed: Jun. 12, 2019

(65) Prior Publication Data

US 2019/0294449 A1 Sep. 26, 2019

Related U.S. Application Data

(63) Continuation of application No. 14/464,091, filed on Aug. 20, 2014, now Pat. No. 10,379,873.
(Continued)

(51) Int. Cl.
*G06F 9/4401* (2018.01)
*A61B 17/00* (2006.01)
(Continued)

(52) U.S. Cl.
CPC ............ *G06F 9/4416* (2013.01); *A61B 17/00* (2013.01); *G01S 5/0236* (2013.01); *G01S 5/0284* (2013.01);
(Continued)

(58) Field of Classification Search
None
See application file for complete search history.

(56) References Cited

U.S. PATENT DOCUMENTS 5,414,812 A 5/1995 Filip et al.
5,727,055 A 3/1998 Ivie et al.
(Continued)

FOREIGN PATENT DOCUMENTS

CN 1217078 A 5/1999
CN 1672060 A 9/2005
(Continued)

OTHER PUBLICATIONS

Liang, "Social Network Service," Mar. 31, 2013, pp. 137-138.
(Continued)

*Primary Examiner* — Chris Parry
*Assistant Examiner* — Abderrahmen Chouat
(74) *Attorney, Agent, or Firm* — Foley & Lardner LLP

(57) ABSTRACT

A distributed device network including a number of device nodes connected to a wireless mesh network and including memory configured to store instructions thereon. The instructions cause the one or more processors to receive, from a server by a first device node of the number of device nodes, a first packaged application, the first packaged application including a first functionality, execute, by the first device node, the first packaged application to provide the first functionality receive, from the server by a second device node of the number of device nodes, a second packaged application, the second packaged application including a second functionality, execute, by the second device node, the second packaged application to provide the second functionality, wherein the number of device nodes are resource-constrained devices that cooperate to perform one or more functions of a cloud computing system.

20 Claims, 8 Drawing Sheets

Related U.S. Application Data

(60) Provisional application No. 61/973,962, filed on Apr. 2, 2014, provisional application No. 61/946,054, filed on Feb. 28, 2014.

(51) Int. Cl.

| | | |
|---|---|---|
| *G01S 5/02* | (2010.01) | |
| *G01S 13/76* | (2006.01) | |
| *G01S 13/87* | (2006.01) | |
| *G06F 8/61* | (2018.01) | |
| *G08B 7/06* | (2006.01) | |
| *G08B 13/196* | (2006.01) | |
| *G08B 25/00* | (2006.01) | |
| *G08B 29/18* | (2006.01) | |
| *H04L 9/00* | (2022.01) | |
| *H04L 12/46* | (2006.01) | |
| *H04L 12/64* | (2006.01) | |
| *H04L 43/0876* | (2022.01) | |
| *H04L 61/106* | (2022.01) | |
| *H04L 67/00* | (2022.01) | |
| *H04L 67/104* | (2022.01) | |
| *H04L 67/12* | (2022.01) | |
| *H04N 5/76* | (2006.01) | |
| *H04N 23/65* | (2023.01) | |
| *H04W 8/26* | (2009.01) | |
| *H04W 16/26* | (2009.01) | |
| *H04W 24/02* | (2009.01) | |
| *H04W 88/04* | (2009.01) | |
| *H04L 43/0805* | (2022.01) | |
| *H04L 61/59* | (2022.01) | |
| *H04L 67/1087* | (2022.01) | |
| *H04L 101/672* | (2022.01) | |
| *H04W 4/38* | (2018.01) | |
| *H04W 84/18* | (2009.01) | |
| *H04W 92/02* | (2009.01) | |

(52) U.S. Cl.
CPC .......... *G01S 13/765* (2013.01); *G01S 13/876* (2013.01); *G06F 8/63* (2013.01); *G08B 7/062* (2013.01); *G08B 7/066* (2013.01); *G08B 13/19613* (2013.01); *G08B 13/19634* (2013.01); *G08B 13/19697* (2013.01); *G08B 25/009* (2013.01); *G08B 29/181* (2013.01); *G08B 29/188* (2013.01); *H04L 9/004* (2013.01); *H04L 12/4625* (2013.01); *H04L 12/6418* (2013.01); *H04L 43/0876* (2013.01); *H04L 61/106* (2013.01); *H04L 67/104* (2013.01); *H04L 67/12* (2013.01); *H04L 67/34* (2013.01); *H04N 5/76* (2013.01); *H04N 23/65* (2023.01); *H04W 8/26* (2013.01); *H04W 16/26* (2013.01); *H04W 24/02* (2013.01); *H04W 88/04* (2013.01); *G08B 13/19608* (2013.01); *G08B 13/19671* (2013.01); *G08B 25/007* (2013.01); *H04L 43/0805* (2013.01); *H04L 61/59* (2022.05); *H04L 67/1051* (2013.01); *H04L 67/1093* (2013.01); *H04L 2101/672* (2022.05); *H04W 4/38* (2018.02); *H04W 84/18* (2013.01); *H04W 92/02* (2013.01); *Y04S 40/00* (2013.01); *Y04S 40/18* (2018.05)

(56) References Cited

U.S. PATENT DOCUMENTS

| | | |
|---|---|---|
| 6,012,150 A | 1/2000 | Bartfai et al. |
| 6,208,247 B1 | 3/2001 | Agre et al. |
| 6,272,621 B1 | 8/2001 | Key et al. |
| 6,313,549 B1 | 11/2001 | Moisan et al. |
| 6,531,963 B1 | 3/2003 | Nyfelt |
| 6,636,900 B2 | 10/2003 | Abdelnur |
| 6,873,260 B2 | 3/2005 | Lancos et al. |
| 6,888,459 B2 | 5/2005 | Stilp |
| 6,952,574 B2 | 10/2005 | Tealdi et al. |
| 6,970,183 B1 | 11/2005 | Monroe |
| 7,005,971 B2 | 2/2006 | Stewart et al. |
| 7,295,106 B1 | 11/2007 | Jackson et al. |
| 7,327,251 B2 | 2/2008 | Corbett, Jr. |
| 7,474,330 B2 | 1/2009 | Wren et al. |
| 7,535,687 B2 | 5/2009 | Costa |
| 7,688,808 B2 | 3/2010 | Ren et al. |
| 7,756,828 B2 | 7/2010 | Baron et al. |
| 7,855,635 B2 | 12/2010 | Cohn et al. |
| 7,907,753 B2 | 3/2011 | Wilson et al. |
| 7,920,843 B2 | 4/2011 | Martin et al. |
| 7,966,660 B2 | 6/2011 | Yermal et al. |
| 8,089,910 B2 | 1/2012 | Doh et al. |
| 8,149,849 B2 | 4/2012 | Osborn et al. |
| 8,164,443 B2 | 4/2012 | Alston et al. |
| 8,260,893 B1 | 9/2012 | Bandhole et al. |
| 8,305,196 B2 | 11/2012 | Kennedy et al. |
| 8,331,544 B2 | 12/2012 | Kraus et al. |
| 8,350,700 B2 | 1/2013 | Fast et al. |
| 8,395,494 B2 | 3/2013 | Trundle et al. |
| 8,400,268 B1 | 3/2013 | Malik et al. |
| 8,467,763 B2 | 6/2013 | Martin et al. |
| 8,477,687 B2 | 7/2013 | Iwasa |
| 8,487,762 B1 | 7/2013 | McMullen et al. |
| 8,525,665 B1 | 9/2013 | Trundle et al. |
| 8,572,290 B1 | 10/2013 | Mukhopadhyay et al. |
| 8,572,600 B2 | 10/2013 | Chung et al. |
| 8,572,677 B2 | 10/2013 | Bartholomay et al. |
| 8,582,431 B2 | 11/2013 | Johansen |
| 8,587,670 B2 | 11/2013 | Wood et al. |
| 8,611,323 B2 | 12/2013 | Berger et al. |
| 8,630,820 B2 | 1/2014 | Amis |
| 8,634,788 B2 | 1/2014 | Wright et al. |
| 8,643,719 B2 | 2/2014 | Vian et al. |
| 8,644,165 B2 | 2/2014 | Saarimaki et al. |
| 8,659,417 B1 | 2/2014 | Trundle et al. |
| 8,667,571 B2 | 3/2014 | Raleigh |
| 8,675,920 B2 | 3/2014 | Hanson et al. |
| 8,676,930 B2 | 3/2014 | Foisy |
| 8,696,430 B2 | 4/2014 | Wells |
| 8,700,747 B2 | 4/2014 | Spitaels et al. |
| 8,700,749 B2 | 4/2014 | Elliott et al. |
| 8,707,431 B2 | 4/2014 | Stephens et al. |
| 8,731,689 B2 | 5/2014 | Platner et al. |
| 8,732,255 B2 | 5/2014 | Odio et al. |
| 8,732,292 B2 | 5/2014 | Tokunaga et al. |
| 8,737,957 B2 | 5/2014 | Raleigh |
| 8,848,721 B2 | 9/2014 | Turunen et al. |
| 8,989,053 B1 | 3/2015 | Skaaksrud et al. |
| 9,277,352 B1 | 3/2016 | Ward |
| 10,282,852 B1 | 5/2019 | Buibas et al. |
| 2002/0067259 A1 | 6/2002 | Fufidio et al. |
| 2002/0121979 A1 | 9/2002 | Smith |
| 2003/0097464 A1 | 5/2003 | Martinez et al. |
| 2003/0097586 A1 | 5/2003 | Mok |
| 2003/0216144 A1 | 11/2003 | Roese et al. |
| 2004/0017929 A1 | 1/2004 | Bramblet et al. |
| 2004/0027243 A1 | 2/2004 | Carrender |
| 2004/0090329 A1 | 5/2004 | Hitt |
| 2004/0103164 A1 | 5/2004 | Tabuchi et al. |
| 2004/0103165 A1 | 5/2004 | Nixon et al. |
| 2004/0109059 A1 | 6/2004 | Kawakita |
| 2004/0135694 A1 | 7/2004 | Nyfelt |
| 2004/0153671 A1 | 8/2004 | Schuyler et al. |
| 2005/0052281 A1 | 3/2005 | Bann |
| 2006/0022816 A1 | 2/2006 | Yukawa |
| 2006/0035205 A1 | 2/2006 | Dobson et al. |
| 2006/0039356 A1 | 2/2006 | Rao et al. |
| 2006/0047666 A1 | 3/2006 | Bedi et al. |
| 2006/0059557 A1 | 3/2006 | Markham et al. |
| 2006/0143439 A1 | 6/2006 | Arumugam et al. |
| 2006/0240818 A1 | 10/2006 | McCoy et al. |

(56) References Cited

U.S. PATENT DOCUMENTS

| | | |
|---|---|---|
| 2006/0282886 A1 | 12/2006 | Gaug |
| 2007/0028119 A1 | 2/2007 | Mirho |
| 2007/0073861 A1 | 3/2007 | Amanuddin et al. |
| 2007/0093975 A1 | 4/2007 | Hoogenboom |
| 2007/0106775 A1 | 5/2007 | Wong |
| 2007/0112574 A1* | 5/2007 | Greene ........... H04W 12/00407 340/572.1 |
| 2007/0185788 A1 | 8/2007 | Dillon |
| 2007/0186106 A1 | 8/2007 | Ting et al. |
| 2007/0223451 A1 | 9/2007 | Ren et al. |
| 2007/0239350 A1 | 10/2007 | Zumsteg et al. |
| 2007/0248065 A1 | 10/2007 | Banerjea et al. |
| 2007/0252001 A1 | 11/2007 | Kail et al. |
| 2007/0260470 A1 | 11/2007 | Bornhoevd et al. |
| 2008/0002599 A1 | 1/2008 | Yau et al. |
| 2008/0010631 A1 | 1/2008 | Harvey et al. |
| 2008/0056261 A1 | 3/2008 | Osborn et al. |
| 2008/0068150 A1 | 3/2008 | Nguyen et al. |
| 2008/0068267 A1 | 3/2008 | Huseth et al. |
| 2008/0130949 A1 | 6/2008 | Ivanov et al. |
| 2008/0136620 A1 | 6/2008 | Lee et al. |
| 2008/0144587 A1 | 6/2008 | Gupta et al. |
| 2008/0259919 A1 | 10/2008 | Monga |
| 2008/0291017 A1 | 11/2008 | Yermal et al. |
| 2009/0021634 A1 | 1/2009 | Chang |
| 2009/0027225 A1 | 1/2009 | Farley |
| 2009/0135007 A1 | 5/2009 | Donovan et al. |
| 2009/0146833 A1 | 6/2009 | Lee et al. |
| 2009/0222921 A1 | 9/2009 | Mukhopadhyay et al. |
| 2009/0243844 A1 | 10/2009 | Ishidera |
| 2009/0322510 A1 | 12/2009 | Berger et al. |
| 2010/0090829 A1 | 4/2010 | Pujol |
| 2010/0124209 A1 | 5/2010 | In et al. |
| 2010/0217651 A1 | 8/2010 | Crabtree et al. |
| 2010/0226342 A1 | 9/2010 | Colling et al. |
| 2011/0001812 A1 | 1/2011 | Kang et al. |
| 2011/0051656 A1 | 3/2011 | Hethuin et al. |
| 2011/0069687 A1* | 3/2011 | Rezvani ............. H04L 12/6418 370/338 |
| 2011/0102171 A1 | 5/2011 | Raji et al. |
| 2011/0109434 A1 | 5/2011 | Hadsall, Sr. |
| 2011/0137614 A1 | 6/2011 | Wheeler et al. |
| 2011/0310779 A1 | 12/2011 | De Poorter et al. |
| 2011/0310791 A1 | 12/2011 | Prakash et al. |
| 2012/0014567 A1 | 1/2012 | Allegra et al. |
| 2012/0039235 A1 | 2/2012 | Chen et al. |
| 2012/0131115 A1 | 5/2012 | Levell et al. |
| 2012/0158161 A1 | 6/2012 | Cohn et al. |
| 2012/0159579 A1 | 6/2012 | Pineau et al. |
| 2012/0197986 A1 | 8/2012 | Chen et al. |
| 2012/0266168 A1* | 10/2012 | Spivak ................. H04L 47/70 718/1 |
| 2012/0310423 A1 | 12/2012 | Taft |
| 2012/0311614 A1 | 12/2012 | Deanna et al. |
| 2012/0324245 A1* | 12/2012 | Sinha ................. G06F 1/30 713/300 |
| 2013/0003645 A1 | 1/2013 | Shapira et al. |
| 2013/0064233 A1 | 3/2013 | Hethuin et al. |
| 2013/0070745 A1 | 3/2013 | Nixon et al. |
| 2013/0219050 A1* | 8/2013 | Park ................. G06F 16/178 709/224 |
| 2013/0239192 A1 | 9/2013 | Linga et al. |
| 2013/0241744 A1 | 9/2013 | Erdos et al. |
| 2013/0317659 A1* | 11/2013 | Thomas ............... H02J 4/00 700/286 |
| 2013/0318529 A1 | 11/2013 | Bishop et al. |
| 2013/0336230 A1 | 12/2013 | Zou et al. |
| 2013/0346229 A1 | 12/2013 | Martin et al. |
| 2014/0035726 A1 | 2/2014 | Schoner et al. |
| 2014/0052832 A1 | 2/2014 | Dina et al. |
| 2014/0129135 A1 | 5/2014 | Holden et al. |
| 2014/0222892 A1 | 8/2014 | Lee et al. |
| 2015/0074178 A1 | 3/2015 | Hong et al. |
| 2015/0248299 A1 | 9/2015 | Rasband et al. |
| 2015/0249588 A1 | 9/2015 | Leon et al. |
| 2015/0257301 A1 | 9/2015 | Morgan et al. |
| 2016/0277261 A9* | 9/2016 | Ansari .................... H04L 67/51 |
| 2016/0344841 A1* | 11/2016 | Wang ..................... H04L 67/63 |
| 2017/0270722 A1 | 9/2017 | Tse et al. |
| 2018/0107880 A1 | 4/2018 | Danielsson et al. |
| 2018/0181794 A1 | 6/2018 | Benini et al. |
| 2019/0043281 A1 | 2/2019 | Aman |

FOREIGN PATENT DOCUMENTS

| | | | |
|---|---|---|---|
| CN | 1871782 | A | 11/2006 |
| CN | 1981313 | A | 6/2007 |
| CN | 101067843 | A | 11/2007 |
| CN | 101199187 | A | 6/2008 |
| CN | 101364734 | A | 2/2009 |
| CN | 101764759 | A | 6/2010 |
| CN | 101951341 | A | 1/2011 |
| CN | 101976377 | A | 2/2011 |
| CN | 101977124 | A | 2/2011 |
| CN | 102035738 | A | 4/2011 |
| CN | 102316053 | A | 1/2012 |
| CN | 102325075 | A | 1/2012 |
| CN | 202475489 | U | 10/2012 |
| CN | 103139019 | A * | 6/2013 |
| EP | 0 814 393 | | 12/1997 |
| EP | 1 885 039 | | 2/2008 |
| JP | 2005-292942 | A | 10/2005 |
| JP | 2008-090861 | A | 4/2008 |
| WO | WO-01/06401 | A1 | 1/2001 |
| WO | WO-01/26329 | A2 | 4/2001 |
| WO | WO-2004/068855 | A1 | 8/2004 |
| WO | WO-2008/139203 | | 11/2008 |
| WO | WO-2009/017687 | A1 | 2/2009 |
| WO | WO-2009/079036 | A1 | 6/2009 |
| WO | WO-2013/091678 | A1 | 6/2013 |
| WO | WO-2013/159217 | A1 | 10/2013 |

OTHER PUBLICATIONS

Office Action on CN 201580022068.2, dated Aug. 26, 2020, 13 pages with English translation.
Office Action on KR 10-2016-7026940, dated Dec. 18, 2020, 8 pages.
Zhou Ying et al., "Mobile Agent-based Policy Management for Wireless Sensor Networks," 2005 International Conference on Wireless Communications, Networking and Mobile Computing, Sep. 26, 2005, 4 pages.
Office Action on KR 10-2016-7026962, dated Dec. 18, 2020, 3 pages.
U.S. Appl. No. 61/946,054, filed Feb. 28, 2014, Rasband et al.
U.S. Appl. No. 61/973,962, filed Apr. 2, 2014, Hall et al.
Asada et al, Wireless Integrated Network Sensors (WINS) Proceedings of the Spie, Spie, Bellingham, VA, vol. 3673, dated Mar. 1, 1999, pp. 11-18.
Chen et al., Enix: a lightweight dynamic operating system for tightly constrained wireless sensor platforms, Proceedings of the 8th ACM Conference on Embedded Networked Sensor Systems, dated Nov. 3, 2010, 14 pages. http://sensys.acm.org/2010/Papers/p183-Chen.pdf.
Cheng, Research on AODV Routing Protocol of Wireless Network, Chinese Master's Theses Full-Text Database, Information Technology Division, dated Jul. 15, 2007, pp. 20-58.
Depoorter, Eli, et al., Enabling Direct Connectivity Between Heterogeneous Objections in the Internet of Things Through a Network Service Oriented Architecture, http://jwcn.eurasigjournals.com/content/pdf/1687-1499-2011-61.pdf, dated Aug. 31, 2011, 14 pages.
European Search Report on EP 15755714, dated Oct. 25, 2017, 11 pages.
European Search Report on EP 15756099, dated Oct. 26, 2017, 19 pages.
Extended European Search Report on EP 15755330.6, dated Oct. 25, 2017, 11 pages.
Gopinath et al, A Gateway Solution for IPV6 Wireless Sensor Networks, International Conference on Ultra Modern Communications (ICUMT), Oct. 12-14, 2009, IEEE, pp. 1-6.

(56) References Cited

OTHER PUBLICATIONS

Hill et al, The Platforms Enabling Wireless Sensor Networks, Communications of the ACM, dated Jun. 2004, vol. 47, No. 6, 6 pages.
International Extended Search Report on Application No. PCT/US00/27515, dated Oct. 18, 2001, 14 pages.
International Search Report and Written Opinion on Application No. PCT/US15/17491, dated Jun. 10, 2015, 16 pages.
International Search Report and Written Opinion on Application No. PCT/US15/17680, dated Jun. 24, 2015, 12 pages.
International Search Report and Written Opinion on Application No. PCT/US15/17688, dated Jun. 8, 2015, 10 pages.
International Search Report and Written Opinion on Application No. PCT/US15/17696 dated Jun. 8, 2015, 12 pages.
International Search Report and Written Opinion on Application No. PCT/US15/17702 dated Jun. 17, 2015, 16 pages.
International Search Report and Written Opinion on Application No. PCT/US15/17924, dated Jun. 5, 2015, 7 pages.
International Search Report and Written Opinion on Application No. PCT/US15/17931 dated Jun. 10, 2015, 11 pages.
International Search Report and Written Opinion on Application No. PCT/US2015/017212, dated Jun. 2, 2015.
International Search Report and Written Opinion on Application No. PCT/US2015/017212, dated Jun. 2, 2015, 10 pages.
International Search Report and Written Opinion on Application No. PCT/US2015/017221, dated May 26, 2015, 11 pages.
International Search Report and Written Opinion on PCT/US15/017450, dated Jun. 10, 2015, 6 pages.
International Search Report and Written Opinion on PCT/US15/017477, dated Jun. 10, 2015, 7 pages.
International Search Report and Written Opinion on PCT/US15/017481, dated Jun. 10, 2015, 6 pages.
International Search Report and Written Opinion on PCT/US15/017491, dated Jun. 10, 2015, 6 pages.
International Search Report and Written Opinion on PCT/US15/024050, dated Jul. 20, 2015, 8 pages.
International Search Report and Written Opinion on PCT/US2015/017212, dated Jun. 2, 2015, 10 pages.
International Search Report and Written Opinion on PCT/US2015/017221, dated May 26, 2015, 11 pages.
International Search Report and Written Opinion on PCT/US2015/017491, dated Jun. 10, 2015, 15 pages.
International Search Report and Written Opinion on PCT/US2015/017924, dated Jun. 5, 2015, 12 pages.
International Search Report and Written Opinion on PCT/US2015/017931, dated Jun. 10, 2015, 11 pages.
Office Action on CN 201580013943.0, dated Mar. 21, 2019, 20 pages with translation.
Office Action on CN 201580013946.4, dated May 8, 2019, 9 pages with translation.
Office Action on CN 201580013946.4, dated Jul. 31, 2018, 13 pages with translation.
Office Action on CN 201580015274.0, dated Feb. 3, 2019, 13 pages with translation.
Office Action on CN 201580015274.0, dated Jul. 3, 2019, 11 pages with translation.
Office Action on CN 201580015282.5, dated Sep. 4, 2018, 18 pages with translation.
Office Action on CN 201580016167.X, dated May 2, 2018, 20 pages with translation.
Office Action on CN 201580016948.9, dated May 25, 2018. 24 pages with translation.
Office Action on CN 201580019382.5, dated Jul. 31, 2019, 17 pages with translation.
Office Action on CN 201580019386.3, dated Jun. 4, 2019, 34 pages with translation.
Office Action on CN 201580019691.2, dated Apr. 29, 2019, 15 pages with translation.
Office Action on Cn 201580019697.X, dated Feb. 26, 2019, 20 pages with translation.
Office Action on CN 201580020164.3 dated Mar. 27, 2019, 24 pages with translation.
Office Action on CN 201580021841.3, dated Jun. 26, 2019, 16 pages with translation.
Office Action on CN 201580026024.7, dated Jun. 4, 2019, 12 pages with translation.
Office Action on EP 15754691.2, dated May 10, 2019, 5 pages.
Office Action on EP 15754909.8, dated May 20, 2019, 6 pages.
Office Action on EP 15754909.8, dated Sep. 11, 2018, 5 pages.
Office Action on EP 15755018.7, dated Jul. 9, 2019, 6 pages.
Office Action on EP 15755018.7, dated Sep. 11, 2018, 5 pages.
Office Action on EP 15755117.7, dated Aug. 9, 2019, 6 pages.
Office Action on EP 15755117.7, dated Oct. 4, 2018, 6 pages.
Office Action on EP 15755330.6, dated Jun. 19, 2019, 6 pages.
Office Action on EP 15755330.6, dated Oct. 1, 2018, 5 pages.
Office Action on EP 15755456.9, dated Mar. 7, 2019, 5 pages.
Office Action on EP 15755880.0, dated Jan. 30, 2019, 5 pages.
Office Action on JP 2016-560736, dated Feb. 5, 2019, 5 pages with translation.
Supplementary European Search Report on 15754909.8, dated Nov. 7, 2017, 10 pages.
Supplementary European Search Report on EP 15754818.1, dated Dec. 14, 2017, 8 pages.
Supplementary European Search Report on EP 15755117.7, dated Nov. 7, 2017, 10 pages.
Supplementary European Search Report on EP 15755417.1, dated Oct. 23, 2017, 14 pages.
Supplementary European Search Report on EP 15756099.6, dated Oct. 26, 2017, 18 pages.
Supplementary European Search Report on EP 15774423, dated Nov. 17, 2017, 1 page.
Zhou, Ying et al., "Mobile Agent-based Policy Management for Wireless Sensor Networks,", Wireless Communications, Networking and Mobile Computing, 2005, Proceedings 2005 Int'l Conference on Wuhan, China, vol. 2, Sep. 23, 2005, pp. 1207-1210.
EPO Extended Search Report dated Jul. 13, 2020—App No. 20168200.2-1213.
Extended European Search Report on EP 20168200.2, dated Jul. 13, 2020, 11 pages.
Office Action on CN 201580021841.3, dated Mar. 16, 2020, 10 pages with English language translation.
Search Report on EP Application No. 15754818.1 dated Dec. 19, 2019, 6 pages.
Eugster et al., "The many faces of publish/subscribe," ACM computing surveys (CSUR) 35.2, 2003, pp. 114-131.
Hunkeler et al., "MQTT-S—A publish/subscribe protocol for Wireless Sensor Networks," 2008 3rd International Conference on Communication Systems Software and Middleware and Workshops (COMSWARE'08), IEEE, 8 pages.
Zoumboulakis et al., "Active rules for sensor databases," Proceedings of the 1st international workshop on Data management for sensor networks, in conjunction with VLDB 2004, ACM, 2004, 6 pages.

* cited by examiner

DISTRIBUTED PROCESSING SYSTEM

CROSS-REFERENCE TO RELATED PATENT APPLICATIONS

This application is a continuation of U.S. patent application Ser. No. 14/464,091, filed on Aug. 20, 2014, entitled: "Distributed Processing System", which claims priority to provisional U.S. Patent Application No. 61/946,054, filed on Feb. 28, 2014, entitled: "Wireless Sensor Network", and provisional U.S. Patent Application No. 61/973,962, filed on Apr. 2, 2014, entitled: "Wireless Sensor Network", the entire contents of which are incorporated by reference herein.

BACKGROUND

This specification relates generally to a distributed processing system. Wireless sensor network/wireless device based data collection and control systems having remote server-based monitoring and report generation are used in applications such as home safety monitoring, electrical and water utility meter monitoring, and human and asset tracking. For example, it is common for businesses and homeowners to have a security system for detecting alarm conditions at their premises and for signaling conditions to a monitoring station or to authorized users of the security system.

SUMMARY

One embodiment of the present disclosure is a distributed device network including a number of device nodes connected to a wireless mesh network and including memory configured to store instructions thereon, that when executed by one or more processors, cause the one or more processors to, receive, from a server by a first device node of the number of device nodes, a first packaged application, the first packaged application including a first functionality, execute, by the first device node, the first packaged application to provide the first functionality, receive, from the server by a second device node of the number of device nodes, a second packaged application, the second packaged application including a second functionality, execute, by the second device node, the second packaged application to provide the second functionality, wherein the number of device nodes are resource-constrained devices that cooperate to perform one or more functions of a cloud computing system, and wherein the wireless mesh network connects to an external network and wherein the number of device nodes continue perform the one or more functions of the cloud computing system if the external network is disconnected.

In some embodiments, the number of device nodes including a package engine, wherein the package engine manages execution of one or more packaged applications. In some embodiments, the one or more packaged applications have no external dependencies. In some embodiments, each of the one or more packaged applications is associated with a function of the one or more functions. In some embodiments, each of the one or more functions is a microservice. In some embodiments, a first function of the one or more functions is a queue function to store information received from one or more end nodes and send the information to one or more of the number of device nodes. In some embodiments, a second function of the one or more functions is a processing function to perform one or more tasks on information received from one or more of the number of device nodes to produce processing results. In some embodiments, a third function of the one or more functions is a database function to store in local memory processing results received from one or more of the number of device nodes.

Another embodiment of the present disclosure is an edge computing system including a server connected to an external network and having a number of packaged applications and a number of resource-constrained device nodes. The number of resource-constrained device nodes connected to a wireless mesh network, the wireless mesh network connected to the external network, the number of resource-constrained device nodes including one or more processors and memory connected to the one or more processors, the memory having instructions stored thereon, that when executed by the one or more processors, cause the one or more processors to receive, from the server, a first packaged application of the number of packaged applications, the first packaged application associated with a first functionality, execute the first packaged application to provide the first functionality, receive, from the server, a second packaged application of the number of packaged applications, the second packaged application associated with a second functionality, and execute the second packaged application to provide the second functionality, wherein the number of resource-constrained device nodes cooperate to form a cloud computing system providing one or more functions, wherein the number of resource-constrained device nodes continue to provide the one or more functions if the external network is disconnected.

In some embodiments, the number of resource-constrained device nodes including a package engine, wherein the package engine manages execution of the number of packaged applications. In some embodiments, the number of packaged applications have no external dependencies. In some embodiments, each of the number of packaged applications is associated with a function of the one or more functions. In some embodiments, each of the one or more functions is a microservice for the cloud computing system. In some embodiments, a first function of the one or more functions is a queue function to store information received from at least one of a resource-constrained device node of the number of resource-constrained device nodes, or an end node. In some embodiments, a second function of the one or more functions is a processing function to perform one or more tasks on information received from at least one of a resource-constrained device node of the number of resource-constrained device nodes, or an end node, and produce processing results. In some embodiments, a third function of the one or more functions is a database function to store processing results received from one or more resource-constrained device nodes of the number of resource-constrained device nodes.

Another embodiment of the present disclosure is a system including a server connected to an external network and having a number of packaged applications, wherein the number of packaged applications are microservices having no external dependencies, and a number of device nodes forming a wireless mesh network, the wireless mesh network connected to the external network, the number of device nodes including a package engine, one or more processors, and memory connected to the one or more processors, the memory having instructions stored thereon, that when executed by the one or more processors, cause the package engine to receive, from the server, a first packaged application of the number of packaged applications, the first packaged application associated with a first functionality, execute the first packaged application to provide the first functionality, receive, from the server, a second packaged application of the number of packaged applications, the second packaged application associated with a second functionality, and execute the second packaged application to provide the second functionality, wherein the number of packaged applications are associated with one or more functions of a cloud computing system, and wherein the number of device nodes continue to provide the one or more functions if the external network is disconnected.

In some embodiments, a first function of the one or more functions is a queue function to store information received from a source and send the information to a destination. In some embodiments, a second function of the one or more functions is a processing function to perform one or more tasks on the information and produce processing results. In some embodiments, a third function of the one or more functions is a database function to store the processing results.

Any two or more of the features described in this specification, including this summary section, may be combined to form implementations not specifically described herein.

All or part of the foregoing may be implemented as a computer program product comprised of instructions that are tangibly stored on one or more non-transitory machine-readable storage media/hardware devices, and which are executable on one or more processing devices. All or part of the foregoing may be implemented as an apparatus, method, or network system that may include one or more processing devices and memory to store executable instructions to implement functionality.

The details of one or more examples are set forth in the accompanying drawings and the description below. Further features, aspects, and advantages will become apparent from the description, the drawings, and the claims.

DETAILED DESCRIPTION

Described herein are examples of network features that may be used in various contexts including, but not limited to, security/intrusion and alarm systems. Example security systems may include an intrusion detection panel that is electrically or wirelessly connected to a variety of sensors. Those sensors types may include motion detectors, cameras, and proximity sensors (used, e.g., to determine whether a door or window has been opened) or whether a body has moved passed or within sensing range of the proximity sensor. Typically, such systems receive a relatively simple signal (electrically open or closed) from one or more of these sensors to indicate that a particular condition being monitored has changed or become unsecure.

For example, typical intrusion systems can be set-up to monitor entry doors in a building. When a door is secured, a proximity sensor senses a magnetic contact and produces an electrically closed circuit. When the door is opened, the proximity sensor opens the circuit, and sends a signal to the panel indicating that an alarm condition has occurred (e.g., an opened entry door).

Data collection systems are becoming more common in some applications, such as home safety monitoring. Data collection systems employ wireless sensor networks and wireless devices, and may include remote server-based monitoring and report generation. As described in more detail below, wireless sensor networks generally use a combination of wired and wireless links between computing devices, with wireless links usually used for the lowest level connections (e.g., end-node device to hub/gateway). In an example network, the edge (wirelessly-connected) tier of the network is comprised of resource-constrained devices with specific functions. These devices may have a small-to-moderate amount of processing power and memory, and may be battery powered, thus requiring that they conserve energy by spending much of their time in sleep mode. A typical model is one where the edge devices generally form a single wireless network in which each end-node communicates directly with its parent node in a hub-and-spoke-style architecture (also known as a star network topology). The parent node may be, e.g., an access point on a gateway or a sub-coordinator which is, in turn, connected to the access point or another sub-coordinator.

Figure 1:
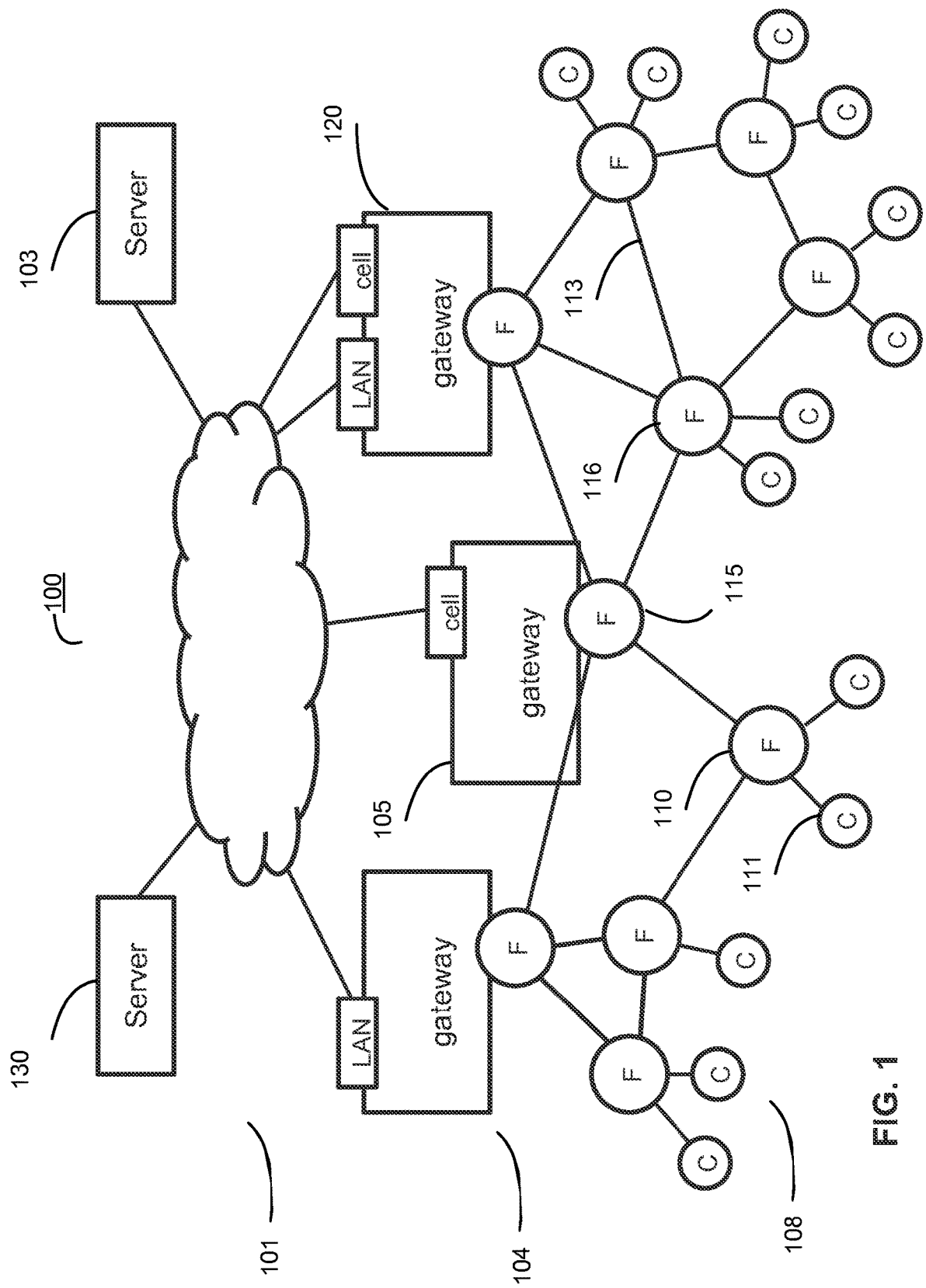
FIG. 1 is a schematic diagram of an example networked security system.

FIG. 1 shows an example (global) distributed network topology 100 for an example Wireless Sensor Network (WSN). In example network topology 100, upper tier 101 of the network may include traditional servers 103 and/or virtual servers running in a "cloud computing" environment and networked using appropriate networking technologies such as Internet connections. Applications running on those servers may communicate using XML/SOAP, RESTful web service, and/or other appropriate application layer technologies such as HTTP and ATOM.

In example network topology 100, middle tier 104 may include gateways 105 located at central, convenient places inside individual buildings and structures. Such gateways may communicate with the upper tier servers and cloud applications using web programming techniques or other appropriate technologies. These gateways 105 communicate with servers 103 in the upper tier whether the servers are stand-alone dedicated servers and/or cloud based servers running cloud applications using web programming techniques. The middle tier gateways 105 are also shown with both local area network (e.g., Ethernet or 802.11) and cellular network interfaces.

In example network topology 100, lower tier (edge layer) 108 may include fully-functional sensor nodes 110 (wireless devices, marked in FIG. 1 with "F") and constrained wireless sensor nodes or sensor end nodes 111 (marked in FIG. 1 with "C"). In some implementations, each gateway may be equipped with an access point (fully functional node or "F" node) physically attached thereto, which provides a wireless connection point to the other nodes in the wireless network.

Constrained computing devices as used herein are devices with substantially less persistent and volatile memory than other computing devices, such as sensors in a detection system. Currently examples of constrained devices would be those with less than about a megabyte of flash/persistent memory, and less than 10-20 kilobytes (KB) of RAM/volatile memory). These constrained devices are configured in this manner; generally due to cost/physical configuration considerations.

In a typical network, the edge (wirelessly-connected) tier of the network is largely comprised of highly resource-constrained devices with specific functions, organized into sub-networks each of which is administered by a fully functional wireless node acting as sub-coordinator (i.e., coordinator of the sub-network). The end-node/constrained devices have a small-to-moderate amount of processing power and memory, and often are battery powered, thus requiring that they conserve energy by spending much of their time in sleep mode. A typical model is one where the edge devices generally form a single wireless network in which each end-node communicates directly with its parent node in a hub-and-spoke-style architecture. The parent node may be, e.g., an access point on a gateway or a sub-coordinator which is, in turn, connected to the access point or another sub-coordinator.

In example network topology 100, the communication links (illustrated by lines 113) shown in FIG. 1 are direct (single-hop network layer) connections between devices. A formal networking layer (that may function in each of the three tiers shown in FIG. 1) can use a series of these links, together with appropriate routing technology, to send messages (fragmented or unfragmented) from one device to another, over a physical distance. In other network topologies, each link may represent two or more hops and/or the configuration may be different than shown in FIG. 1.

In some example implementations, WSN state function based application layer uses an edge device operating system (not shown, but such as disclosed in the above mentioned provisional application) that allows for loading and execution of individual functions (after the booting of the device) without rebooting the device (so-called "dynamic programming"). In other implementations, edge devices could use other operating systems provided such systems allow for loading and execution of individual functions (after the booting of the device) preferable without rebooting of the edge devices.

Example distributed network topology 100 may include or be part of a self-organizing network, such as a wireless mesh network. In some implementations, all of distributed network topology 100 is implemented using wireless mesh technology. In some implementations, only part of distributed network topology 100 is implemented using wireless mesh technology. For example, in FIG. 1, in some implementations, upper tier 101 may be implemented using standard network technology, and middle tier 104 and lower tier 108 may be implemented as one or more wireless mesh networks. In some implementations, upper tier 101 and middle tier 104 may be implemented using standard network technology, and lower tier 108 may be implemented using one or more wireless mesh networks. For example, a different wireless mesh network may be associated with each gateway, or a single wireless mesh network may include all of the gateways shown in FIG. 1 (and others), as well as all or some functional and sensor nodes.

In some implementations, wireless mesh network is a self-organizing wireless network, in which the network devices themselves establish communication links with one another. The communication links may be established by maintaining and updating routing tables associated with each network device. In the example implementations described herein, a wireless mesh network may be established between sensor, functional and/or gateway devices that are part of a larger building, or enterprise-wide system. In examples, such devices may be used for monitor and/or control in a security/intrusion, fire alarm, or other appropriate system. The devices report status information from their systems to a central monitoring service, which may include one or more host computing devices. For example, the central monitoring service may include server 103 and/or server 130, in addition to other computing equipment. The central monitoring service may also send control commands, which the devices use for configuration and/or control.

Figure 2:
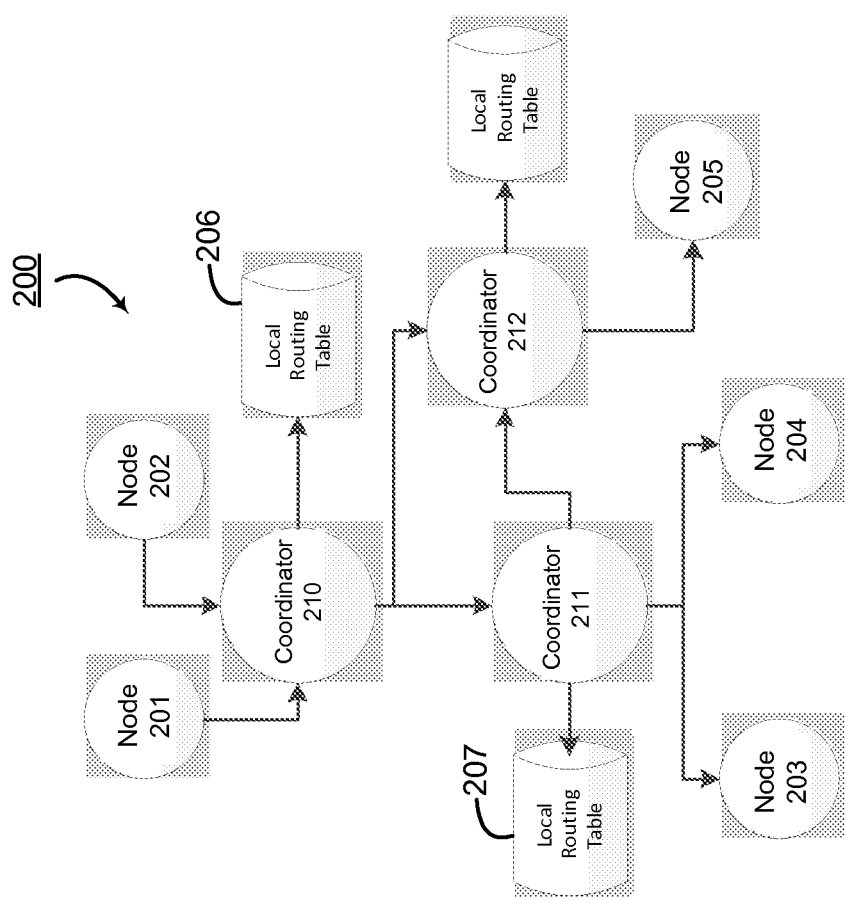
FIG. 2 is a block diagram of a portion of the networked security system of FIG. 1.

FIG. 2 shows components of an example wireless network 200 on which the processes described herein may be implemented. In the implementations described herein, wireless network 200 is a wireless mesh network, and may be part of the larger network shown in FIG. 1. However, in other implementations, the processes described herein may be performed using other types of networks.

Wireless network 200 may be a heterogeneous network, in which devices on wireless network 100 do not perform the same functions, or a homogeneous network, in which devices on wireless network 100 perform the same functions or substantially the same functions. Wireless network 100 includes nodes 201 to 205, which may, or may not, be endpoint devices on the network, such as sensors, monitors or the like. Typically, the primary connection between a node and the network is wireless; however, one or more of nodes 201 to 205 may also include a wired connection to network 200.

Wireless network 200 also includes coordinator devices 210 to 212, which may be intermediary devices on the network. In the example implementations described herein, a coordinator device, e.g., coordinator device 210, functions in its role in the networking layer as a router or repeater to forward data packets sent by a node, e.g., node 201 or node 204 (which need not be a directly connected node) or by another coordinator device, e.g., coordinator 211, along a path through wireless network 200. The coordinators 210-212 communicate with each other to maintain and update routing information to enable communication between devices, and to account for changes in the network 200. The coordinator devices store routing information, such as a next hop along a network path to a data packet's intended destination, and a hop on a return path. This information is stored in one or more local routing table(s) (e.g., local routing table 206, 207, 208) in memory on, or otherwise accessible to, the corresponding coordinator device. In some implementations, the nodes may also include one or more such routing table(s), particularly if the nodes are, or may become part of, a network pathway. The processes described herein may be used to build, and update, those routing tables, along with routing tables on any other appropriate network devices.

Nodes 201 to 205 and coordinator devices 210 to 212 may communicate via radio frequency (RF) links using any appropriate wireless protocol or protocols. Wireless network 200 may also include other types of devices (not shown), such as computers, base stations, or embedded processing devices that interact with the devices of FIG. 2.

Nodes 201 to 205 may each be either a source or a destination of network data. In some implementations, the nodes constitute, or are to, one or more sensors or controlling devices. The sensors are part of physical systems, such as an alarm system or a security system, as noted above, and sense or monitor physical quantities, such as temperature, movement, or the like. A node acquires analog and/or digital signals as a result of this sensing and transmit data packets corresponding to these signals to an appropriate device via wireless network 200. An antenna (not shown) is included on each endpoint device to enable transmission. Antennas are also included on the other wireless devices in the network.

Multiple mesh networks may occupy the same physical space. Data packets for such networks may be differentiated, e.g., by a network group identifier (ID). Thus, the networks remain logically separate even though they occupy the same physical space.

Wireless mesh networks are typically established by one or more prospective network devices initiating communication to one or more other prospective network devices. For example, a first prospective network device (such as node 202) may output a packet identifying the first device (node 202) and in an attempt to locate other devices within the RF vicinity of the first device (node 202), with which the first device may connect. A second prospective network device (such as coordinator device 210) in that vicinity may respond and identify itself as a device that is available for connection to the first device. The two devices may then establish a connection through appropriate back-and-forth communications. This general process, or other(s) like it, may be repeated either by both devices or by other devices until the mesh network is formed. Typically, at least one of the devices is initially in communication with a base station or other wired connection to the central monitoring service, enabling connection between the wireless mesh network and the central monitoring service. Upon connection to the wireless network, routing tables throughout the wireless network may be updated.

Devices may enter, e.g., become part of, a wireless mesh network in the manner described above, or in any other appropriate manner. Likewise, devices may also leave the wireless mesh network. For example, devices may be deactivated or lose power, causing the devices to leave the network. In some cases, loss of a single device may affect communication to numerous other devices on the network. For example, a single device may be the primary pathway over which communications to numerous other devices pass. As a result, loss of that device also interrupts that primary path, necessitating re-routing of communications through the wireless mesh network. This re-routing can affect the contents of routing tables in nodes and coordinators.

The example processes described herein enable routing of data packets through a changing network environment resulting, e.g., from devices entering or leaving the network. This is done by updating configurable routing tables that are distributed across all or some routing nodes in the network. The processes may be used on wireless mesh networks of any size; however, they may have particular applicability to small- to medium-sized networks, in contrast to large wide area networks such as the Internet.

The implementation below is of wireless mesh network 200 updating routing tables based on packet transmissions through node 201 and coordinators 210, 211.

Figure 3:
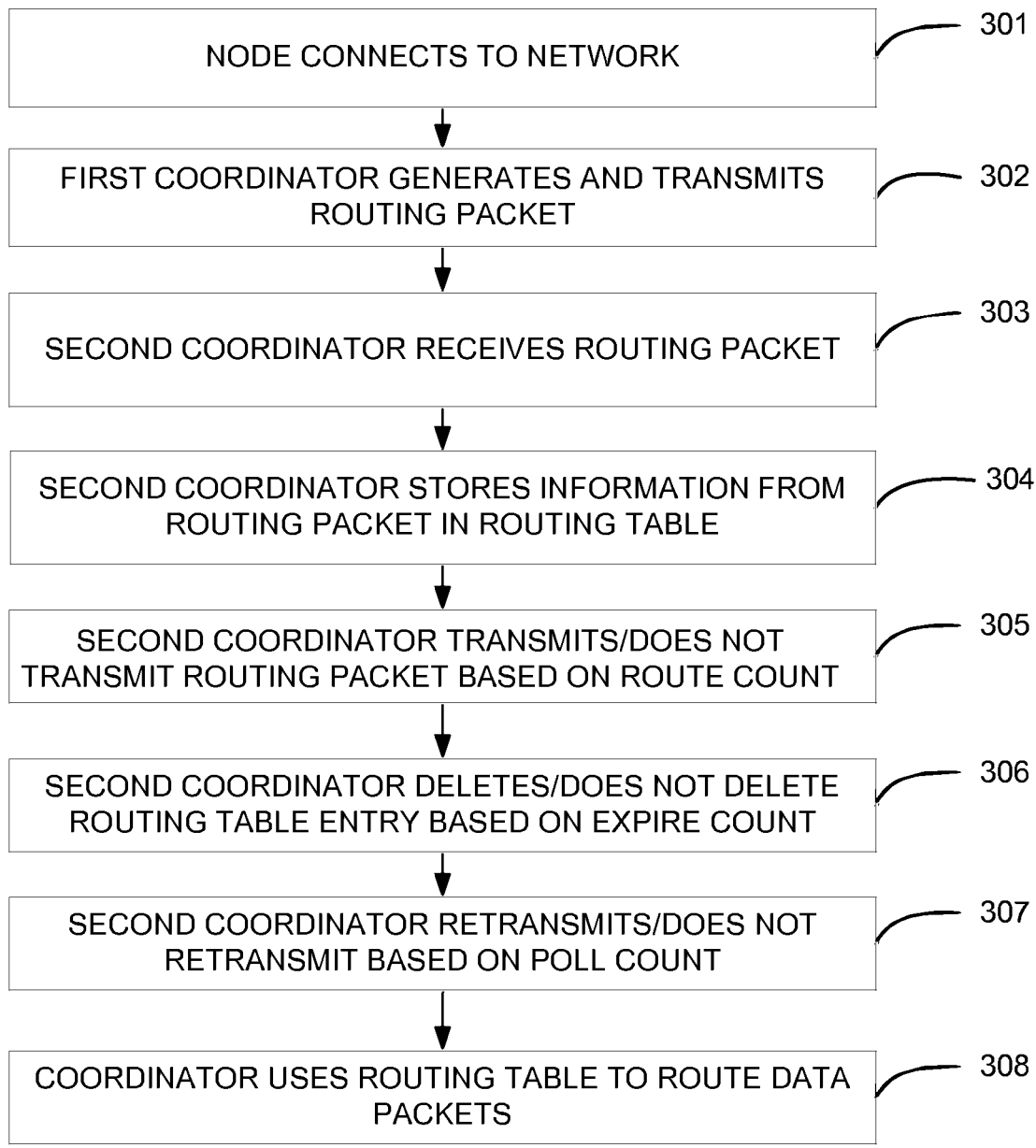
FIG. 3 is a flowchart showing an example process for maintaining routing tables in the network portion of FIG. 2.

Referring to the flowchart of FIG. 3, in this example implementation, a node (such as node 201) connects (301) to a network (such as network 200). Such connection may be implemented in any appropriate manner using one or more processes, e.g., through appropriate communication to coordinator 210. In response, a first coordinator (such as coordinator 210), to which the node has connected, generates and transmits (302) a routing packet containing, in its mesh header (the part of the packet reserved for routing information), the coordinator's short address, the node's short address, and an route count value of zero. In this example, the routing packet is transmitted to advise other devices (e.g., coordinators) in the RF vicinity of the first coordinator of the addition of the node to the network. Information in the routing packet is known to the first coordinator beforehand or is obtained through communication with the node. In this example implementation, a short address is a 2-byte/16-bit random, uniquely-assigned number that identifies a device (either a node, a coordinator, or another network device) within the network. In other implementations, the short address may be replaced by any other appropriate node and/or coordinator identification information. The route count is a value that is incremented at each node (hop), and is used as described below.

A second coordinator, such as coordinator 211, receives (303) the routing packet from coordinator 210. Coordinator 211 checks its routing table entries to determine if information from the routing packet is already present in the routing table. If that information is not already present (which it should not be at this point), coordinator 211 records (e.g., stores) (304), in its routing table 207, a routing entry that includes coordinator 210's short address, node 201's short address, and the route count incremented by one (the route count at coordinator 210 being set at zero). This routing entry is usable by coordinator 211 to route data to/from node 201.

Routing table 207 also stores an "expire count" and a "poll count" for each routing entry in routing table 207. The expire count is a value corresponding to (e.g., equal to) the greatest number of times a route entry will be checked before being deleted from the routing table. The poll count is a value corresponding to (e.g., equal to) the greatest number of times a routing table entry will be checked by a device before routing information for that entry is retransmitted. The values for the expire count and the poll count are either propagated through the network by the coordinators or are hard-coded into the routing table of each device. Other arrangements are possible. Each entry of the routing table may include counters corresponding to the expire count and to the poll count. These counters are incremented by one each time the corresponding routing table entry is checked. The corresponding counter values are compared to the expire count and poll count, and the results of the comparisons are used as described below.

Coordinator 211 performs a check to determine whether the route count incremented by one exceeds a maximum count stored in routing table 207. In this example implementation, the maximum count is a number corresponding to (e.g., equal to) the greatest number of hops through which a packet will be routed.

If the route count does not meet or exceed the maximum count, coordinator 211 transmits (305) the routing packet to other coordinators (such as coordinator 212) that are within its RF vicinity. Otherwise, if the route count meets or exceeds the maximum count, the routing packet is not transmitted. In this regard, if the route count meets or exceeds the maximum count, the maximum number of hops has been reached at coordinator 211. Thus, no further transmission of the routing packet is permitted, which is why the routing packet is not transmitted to another device (e.g., coordinator) on the network. The route count for each routing table entry may be stored in the routing table.

As coordinator 211 checks entries of its routing table 207, the corresponding expire counter and poll counters for entries in routing table 207 are each incremented by one, as described above. If an expire count value reaches the stored expire count, then the corresponding entry in the routing table is deleted (306). As noted, the expire count is a value corresponding to (e.g., equal to) the greatest number of times a route entry will be checked before being deleted from the routing table. Generally, the expire count is used to adjust the network's configuration resulting, e.g., from movement of nodes into or out of the network. If the expire count is reached, the corresponding routing entry is deleted on the assumption that the entry may no longer be valid. Notably, a check is not performed to determine whether the entry is still valid. Rather, the entry is assumed not to be valid any longer, and is deleted. Thus, the system forces the network to reestablish routing pathways after a certain number of checks (look-ups), thereby reducing the number of potentially invalid routes in the routing table.

If the poll count value reaches the stored poll count and the route count for a corresponding routing table entry has a value of zero (e.g., the device is the coordinator to generate the routing packet and thus the first coordinator to transmit the routing packet), then routing information for that entry is re-transmitted (307). This allows for periodic updating of routing table entries from source devices throughout the network.

A coordinator uses the routing table built and maintained in the manner described above to route data packets during normal network operation. For example, when a coordinator (e.g., coordinator 211) receives a regular (e.g., non-routing) data packet having the coordinator's short address in the mesh header, the coordinator uses the destination's short address (also found in the mesh header) to check for, and to identify corresponding values in the routing table, if available. The values may be, e.g., the address of one or more devices on a network path to the data packet's destination. In this example, coordinator 211 performs the check, and obtains the values from its routing table 207. The coordinator then uses the values obtained from its routing tables to re-address the mesh header of the packet to forward the packet to its destination. If the count is zero in the table, then the coordinator fills in the destination address in the mesh header instead of a coordinator address before sending the packet.

The nodes generally and coordinator nodes specifically may be implemented using any appropriate type of computing device, such as a mainframe work station, a personal computer, a server, a portable computing device, or any other type of intelligent device capable of executing instructions, connecting to a network, and forwarding data packets through the network. The nodes generally and coordinator nodes specifically can execute any appropriate computer programs to generate, receive, and transmit data packets for use on the network. Sensing and control nodes" or "end-nodes" are types of "nodes" as used herein. Some physical "nodes" in the network may simultaneously support both "coordinator functions" and "sensing and control functions." In some implementations a single physical device could house the functions of both a "sensing node" and a sub-coordinator.

Each of nodes 201 to 205 and coordinators 210 to 212 may include one or more non-transitory machine-readable media, such as computer memory (not shown), to store executable instructions. Each of these devices may also include one or more processing devices (e.g., microprocessors, programmable logic, application-specific integrated circuits, and so forth) for executing the instructions to perform all or part of the functions described herein. In some implementations, the structure of nodes 201 to 205 may be about the same as the structure of coordinators 210 to 212. This may not be the case in other implementations, e.g., their structures may be different. Each device, however, is programmable to implement appropriate functionality.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

An example, non-limiting application of the WSN of FIGS. 1 to 3 is in a security system for intrusion detection, fire, toxic gas, monitor, etc. installed at one or more premises such as one or more residential houses or building(s) and especially in, e.g., commercial, industrial, buildings, complexes, etc.

In some typical intrusion detection system implementations, an intrusion detection panel is included, whereas in others more sophisticated management systems are included. Sensors/detectors may be disbursed throughout the premises. The intrusion detection system may be in communication with a central monitoring station (also referred to as central monitoring center) via one or more data or communication networks (only one shown), such as the Internet; the phone system, or cellular communication system.

The intrusion detection panel may be configured to receive signals from plural detectors/sensors that send, to the intrusion detection panel, information about the status of the monitored premises. Several types of sensor/detectors (unless otherwise noted are used interchangeably herein) may be used. One type of detector is a detector that sends a binary signal that indicates presence or absence of an event. Examples of these types of detectors include glass break detectors and contact switches. Another type of detector sends metadata that includes information resulting from processing applied by the detector to inputs, e.g., raw data received by the sensor. Examples of these types of detectors may include microphones, motion detectors, smart switches and cameras, recognition devices and so forth.

Some of the detectors and sensors may be hard wired but in general the detectors communicate with systems wirelessly over the WSN. In general, detectors sense glass breakage, motion, gas leaks, fire, and/or breach of an entry point, and send the sensed information over the WSN, as needed and appropriate. Based on the information received from the detectors, the intrusion detection panel determines whether to trigger alarms, e.g., by triggering one or more sirens (not shown) at the premise and/or sending alarm messages to the monitoring station.

As described above with respect to FIGS. 1 to 3, the WSN may include any combination of wired and wireless links that are capable of carrying packet and/or switched traffic, may span multiple carriers and a wide geography, and hay have the features discussed above. In an example implementation, portions of WSN may include the Internet. In another implementation, the WSN may include one or more wireless links, and may include a wireless data network, e.g., with tower such as a 2G, 3G, 4G or LTE cellular data network. The panel may be in communication with the network by way of Ethernet switch or router (not illustrated). The panel may include an Ethernet or similar interface, which may be wired or wireless. Further network components, such as access points, routers, switches, DSL modems, and the like possibly interconnecting the panel with the data network are not illustrated.

The functionality of one or more gateways and/or others of the network devices described above may be distributed among various devices, as described below.

In this regard, in a networking context, the term "cloud" may include a variety of services and applications that reside outside of hardware that is managed or controlled by a user. There are several scenarios that illustrate this concept, such as a website where users access web applications, or an online library where a database resides in a centralized or distributed external location rather than on the user's computers. The traditional architecture for this paradigm is usually a user interface (UI), where the external users connect, via an application program interface (API), to some type of database to manage the information. The user interface submits requests via an API to a cloud server. Typically, each of these requests is processed by modular programs called "agents" or "workers" that run on the cloud-based server, and not in the users' computer. These agents may execute tasks assigned by the users, for example, to query the database or to execute a complex operation involving data and user input.

A new paradigm in device connectivity has been emerging during the past several years. For example, microprocessors embedded in devices are increasingly becoming connected to the Internet so that they can individually provide data about device performance or operating characteristics to remove locations. Many of these devices, such as temperature controllers, smoke detectors, or lighting control switches residing in buildings can be connected wirelessly to a building network, called a wireless sensor network (e.g., a wireless mesh network), and to an external network via a data aggregation and monitoring device called a gateway. In some examples, the gateway collects and aggregates data so that it can be forwarded to the cloud.

The devices, such as temperature controllers, smoke detectors, or lighting control switches, are, or are connected to, end nodes, which may be devices that read sensor data and that connect to a gateway via the sensor network using one or more message routing hops. The gateway aggregates data from these end nodes, and sends that data to the "cloud" server. The cloud may include an external server or cluster of servers that saves the information and is able to respond to user requests. The cloud may also have rules, workers and agents looking (e.g., monitoring) for a particular condition to trigger a specific action.

If the gateway loses communication with the "cloud" server, the functionality of the system may degrade to the point where the nodes become isolated. Each gateway may continue to save sensor data locally until the local memory is full. The capabilities of the system may be reduced by this isolation and the data by itself will not execute action. For example, a door will not be opened in the case of fire because the rules and the decisions are made in the cloud.

Thus, a building could contain dozens of gateways and thousands of end node devices, but with no connection to the cloud, so no action is going to occur. One of the reasons for this situation is the complexity and the scalability of the architecture. Accordingly, described herein is an example of a local architecture that provides the scalability and replication that exists in a typical cloud architecture, but which is deployable on a more resource-constrained system of the gateway and local sensor network. Consequently, in some implementations, the scalability of the cloud system can be duplicated and extended so that the scalability of cloud architecture can be replicated locally at the site location. The databases, the rule engines, the workers, the agents, and queues that are found in a typical cloud architecture require can also be implemented locally (e.g., in the sensor network) using the distributed architecture described herein. Because the processes and distributed architectures have the ability to scale, relatively simple devices like gateways can contain all of (or at least a subset of) the capabilities that exist in the "cloud". As a result, in some cases, the functionality of the "cloud" can continue to operate locally in one or more gateways, despite the absence of connection to an external cloud.

As noted above, in this example, the distributed architecture is scalable, meaning it can be deployed in one device or in thousands of devices in a network. In some examples, the distributed architecture allows the adding of nodes to a cluster and includes no single point of failure. In this example, a cluster includes multiple devices, which may be configured (e.g., programmed) to cooperate to implement a particular functionality.

In some implementations, there is no need for connection to external cloud or, in the case a connectivity failure to the cloud, the example processes described herein allow the gateway or set of gateways to log information amongst themselves, e.g., in one or more distributed local databases. This allows one or more gateways to make decisions using a rule engine that is distributed among the gateways. A feature of this example distributed architecture is that the cloud functionality continues to operate locally among the gateways as long as a single gateway continues to run. In some implementations, this is because of the distribution of the distributed architecture and because the distributed architecture has redundant functionality and, thus, no single point of failure.

Figure 4:
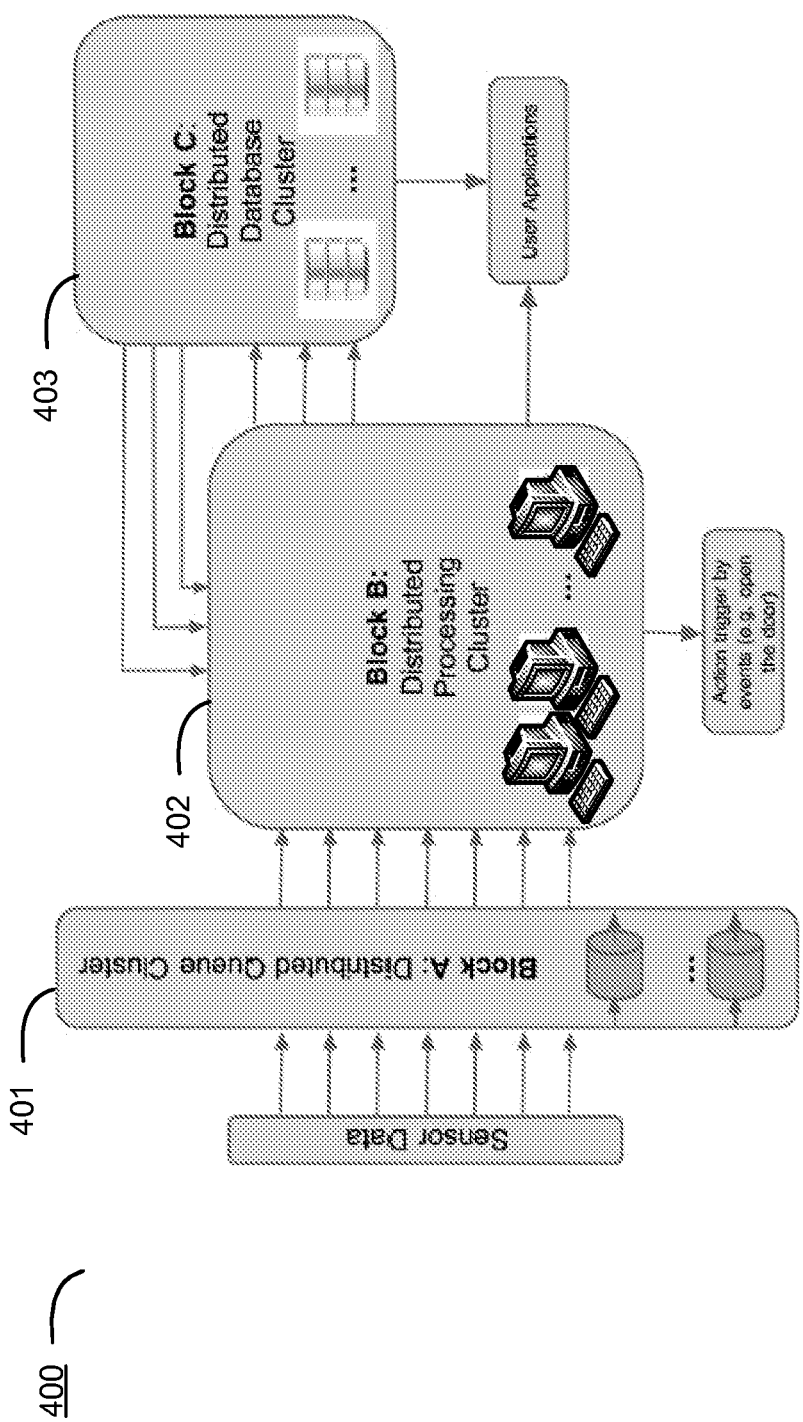
FIG. 4 is a block diagram of an example distributed processing system for use in a sensor network.

FIG. 4 shows a diagram of an example implementation of the distributed architecture 400 described herein. The first block (Block A) 401 of the diagram represents a distributed queue cluster (system). In this example, the queue cluster comprises multiple network devices that cooperate to communicate with end nodes of a network (e.g., node 111 of FIG. 1) and to store information from the end nodes in memory (e.g., one or more hardware storage devices). In operation, communication, represented by messages, comes from sensor data captured at end nodes of the sensor (e.g., wireless mesh) network. The communications are stored in one or more devices in the queue cluster. In this example, every node within the queue cluster presents a RESTful API to the outside world. A purpose of the RESTful API is to decouple, and to allow, any user to communicate with the system in a well-defined interface, avoiding, for instance, a requirement that the user or end device have knowledge the native language of the queue cluster. This cluster or any cluster includes appropriate communication channels between the nodes of the clusters.

The second block on FIG. 4 (Block B) 402 represents an example distributed parallel processing cluster (system). In this example, the processing cluster comprises multiple network devices that cooperate to perform one or more operations on the information from the queue cluster. In this example, this system does not present a single point of failure and all the nodes play the same, or a similar, role. In this example, there are no master or slave nodes. However, in some implementations, there is a leader node that is chosen for one or more tasks (e.g., every task) executed in the processing cluster. The leader node is primarily responsible for execution of the given task, whether it be execution by the leader node itself or coordination of execution among one or more other nodes. When the leader fails, the other nodes agree upon the selection of the new leader for a particular task. This distributed parallel system receives a task or assignment, and can execute a limited task or an unlimited task or until a particular condition occur.

A worker (not shown), which in this example includes a set of rules to act on the data received, may be distributed across the nodes within the cluster according to a replication factor or on demand. When the processing cluster 402 determines that a worker is over-loaded, in this implementation the processing cluster 402 automatically launches more instances of the worker within the cluster of local nodes. In some implementations, the upper limit (e.g., the maximum number of instances) is defined in configuration parameters at the moment when submitting or commissioning a worker to the cluster. In some implementations, there is no upper limit, except as defined by limits of the hardware. The worker can take data from a queue cluster, from other workers, or from a database. The worker stores the result of its processing in a queue cluster, under a given topic, and registers the result in the database cluster or passes the result to another worker The third block (Block C) 403 represents an example distributed database cluster (system) having no single point of failure. The database cluster 403 comprises multiple network devices that cooperate to provide storage for use by the processing cluster. For example, processed data can be stored in the database cluster, data can be retrieved from the database cluster for processing, and so forth. In this example implementation, every node in the data cluster plays the same role in the cluster (no masters no slaves); the database data model is a key-value pair; and a unique key contains a set of values related to the key. In this example, the database also contains a support replication factor per record (value pair, within a key), and a support consistency level per record for writes and reads. In this example, this database exposes a RESTful API and also a native interface when speed is a concern.

The three cluster approach described above forms an example basic distributed architecture 400. In the example implementations described herein, the separation of roles occurs at the function level, rather than at the server level. Accordingly, in the example implementations described herein, every node of the network can become a node of the queue, a node of the processing cluster, or a node of the database cluster at any time and/or at the same time. A physical server can perform the three roles at the same time, which may result in full scalability, from one physical server to hundreds or thousands of servers.

Figure 5:
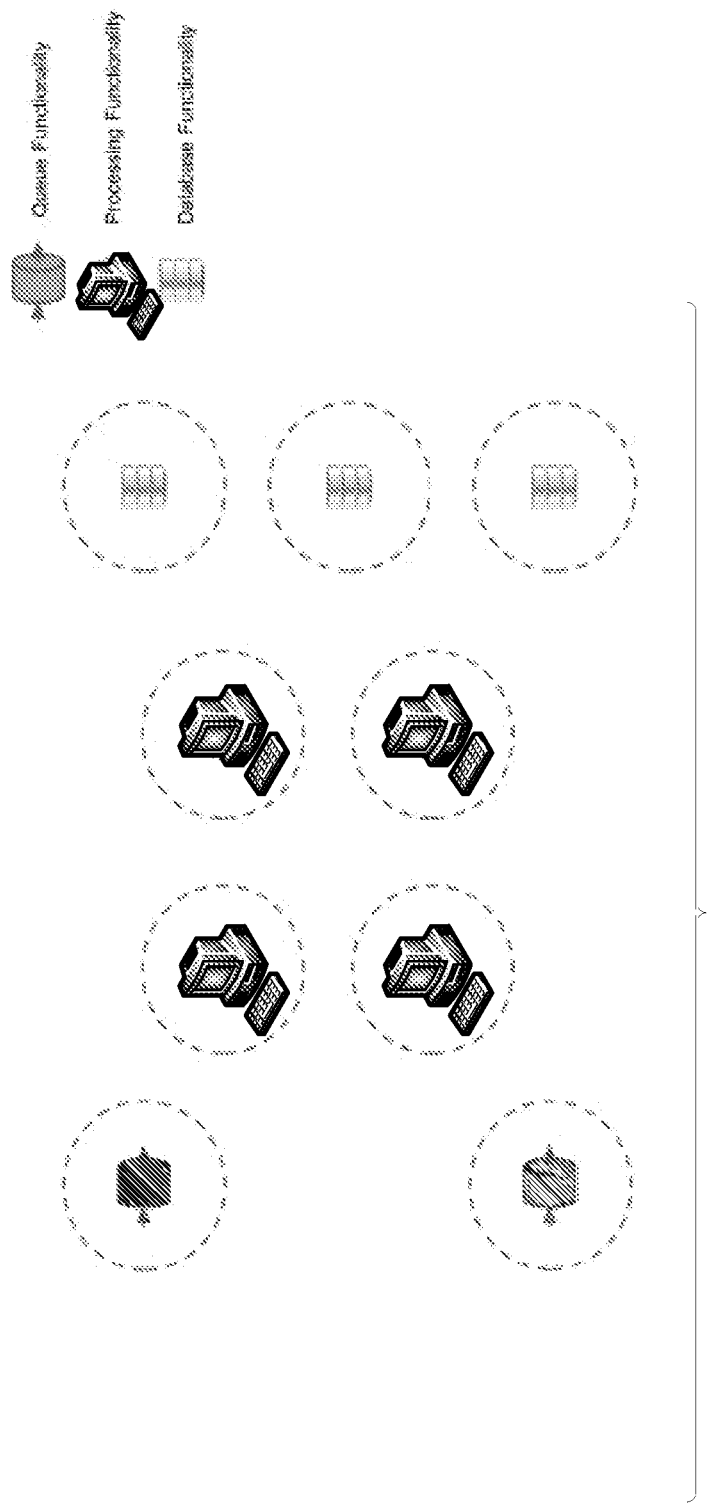
FIG. 5 is a conceptual diagram of a physical server showing different roles (queue, processing, and database) that the physical server performs in the distributed processing system.
Figure 6:
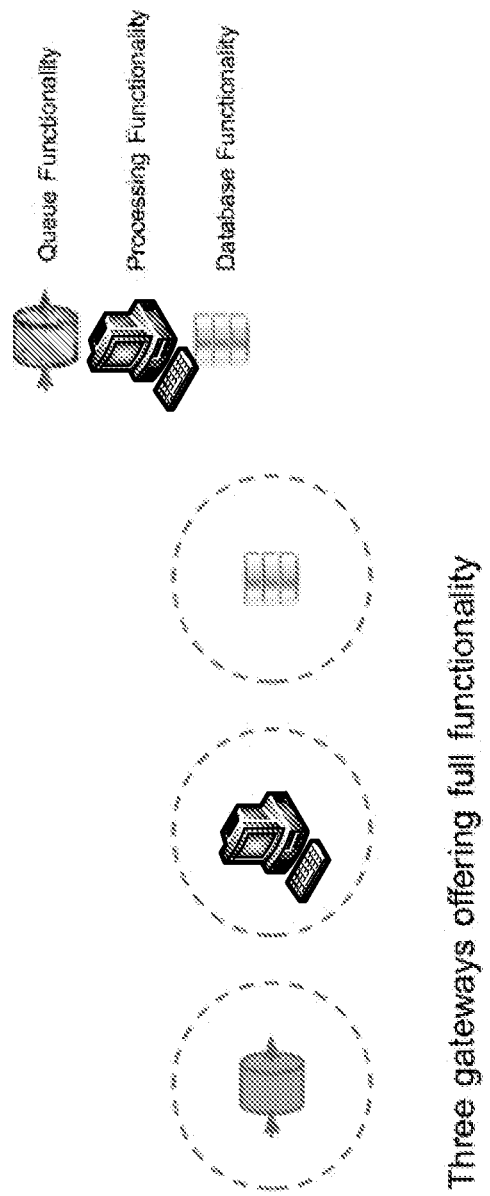
FIG. 6 is a conceptual diagram showing physical servers performing different, single roles in the distributed processing system.
Figure 7:
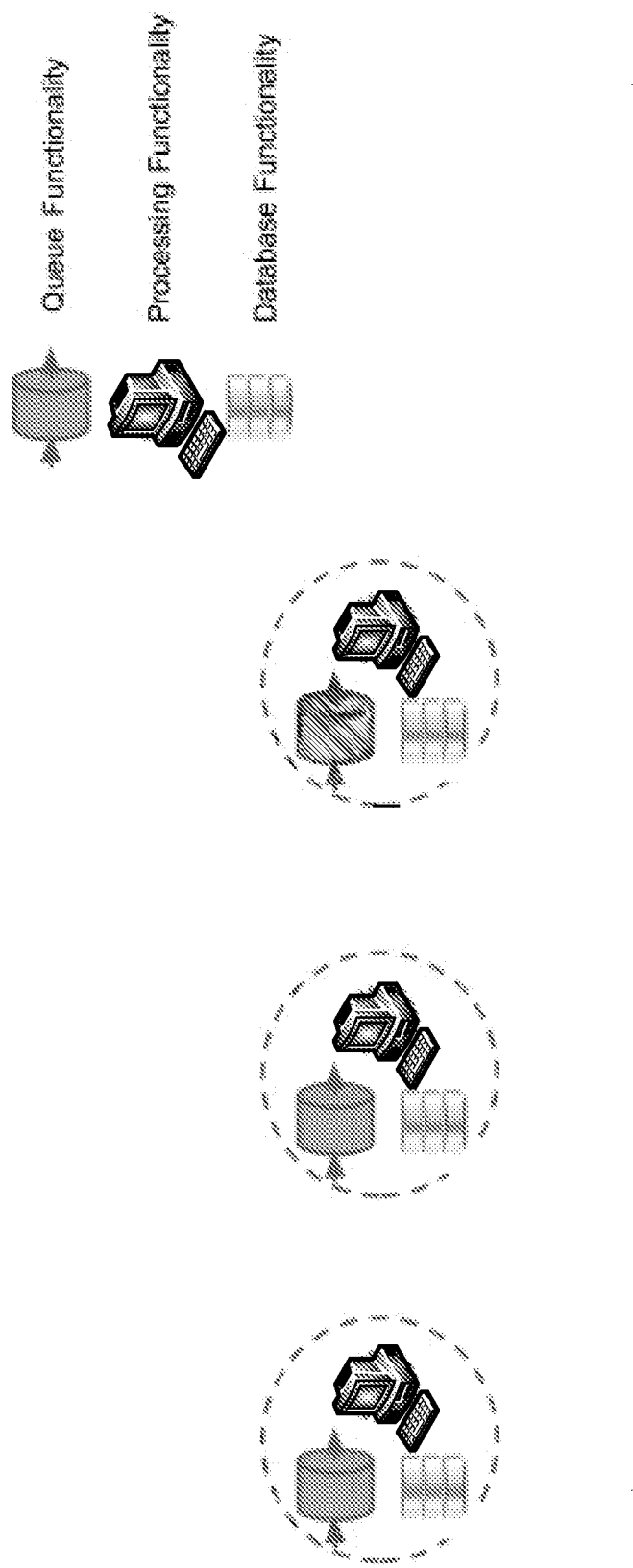
FIG. 7 is a conceptual diagram showing different physical servers each performing multiple different roles in the distributed processing system.

FIGS. 5-7 show, conceptually, different roles (queue, processing, and database) that different physical servers, including gateways that are implemented as servers or other computing devices, may perform at different times. FIG. 5 shows an implementation where a single gateway (e.g., gateway 105 of FIG. 1) is configured to perform the three roles at the same time. The capacity of the gateway may be limited by the processing power of its CPU and a memory capacity of the queue cluster and the database.

FIG. 6 shows an implementation where several gateways are used, and the clusters are defined based on the roles that they perform. For instance, in an example having three gateways, each gateway assumes a different role: one gateway operates as a database, another operates as a queue, and another operates as a processor.

FIG. 7, shows another example implementation, where three gateways operate as a database, a queue, and a processor at the same time. In this example implementation, the failure of one gateway will likely not cause damage to the system since, in this example, two remaining gateways (or even one remaining gateway) can support the system.

In these example implementations, since internal gateways offer cloud services, the connection to an external network ("the cloud") will typically not constitute a point of failure.

Although the processes presented herein are described in the context of communications within a wireless mesh network and to/from an external network such as the Internet, the processes may be used in any appropriate network.

In the example implementations described herein, the queue cluster (Block A of FIG. 4), the distributed processing cluster (Block B of FIG. 4) and, the distributed database cluster (Block C of FIG. 4) may include multiple devices on the network (e.g., nodes, gateways, servers or the like) Each of these network devices may include one or more processing devices (e.g., microprocessors, programmable logic, application-specific integrated circuits, and so forth) for executing the instructions to perform all or part of their corresponding functions described herein. In some implementations, the structure of different devices may be the same or about the same, or the structures of different devices may be different. Each device, however, is programmed with appropriate functionality.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein.

In example implementations, each of the network devices described herein (e.g., including, but not limited to, a server, a gateway, coordinators/sub-coordinators, and end-nodes) may include one or more non-transitory machine-readable media, such as computer memory (not shown), to store executable instructions. Each of the network devices may also include one or more processing devices (e.g., microprocessors, programmable logic, application-specific integrated circuits, and so forth) for executing the instructions to perform all or part of their corresponding functions described herein. In some implementations, the structure of different devices may be the same or about the same, or the structures of different devices may be different. Each device, however, is programmed with appropriate functionality.

Figure 8:
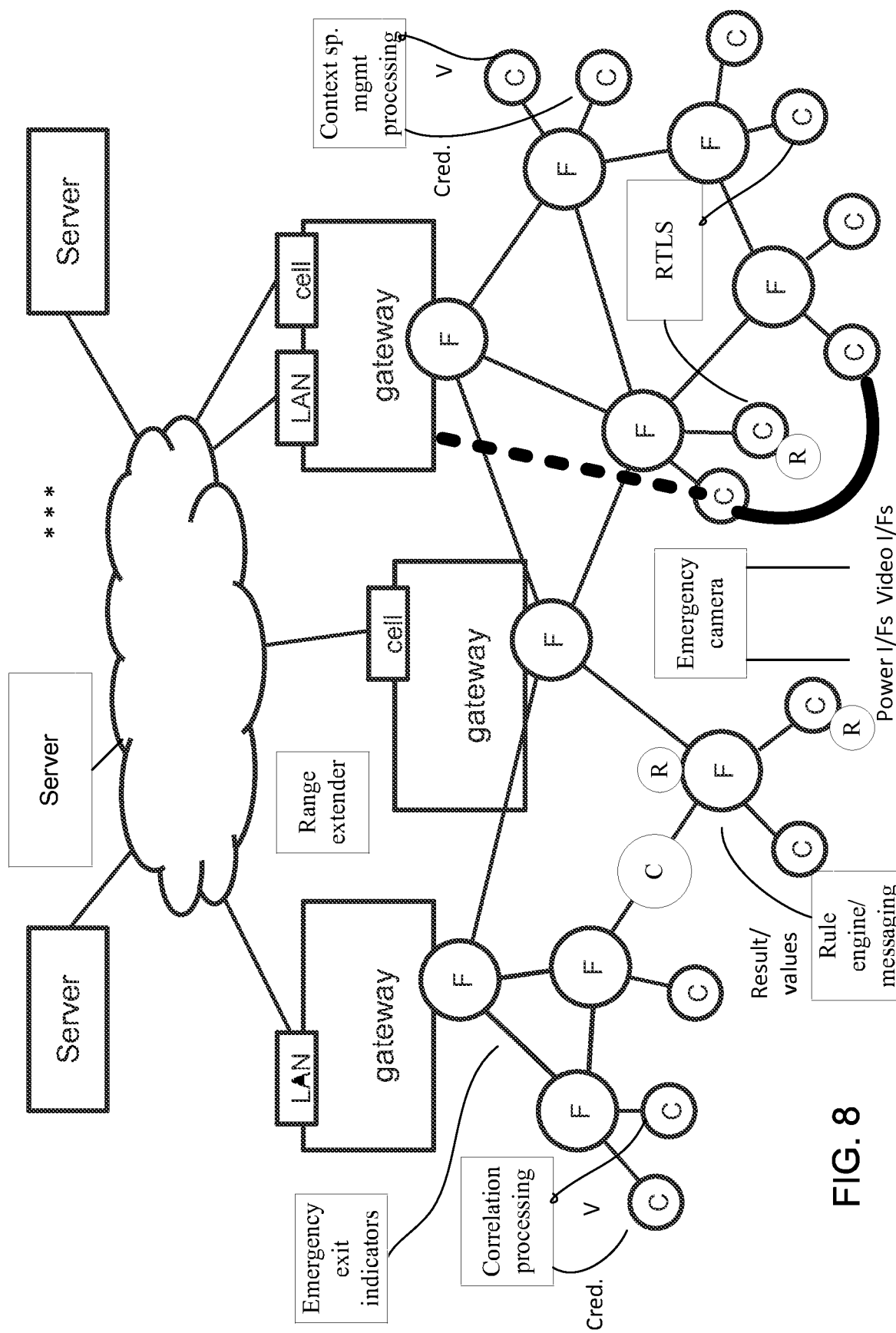
FIG. 8 is a block diagram of components of an example networked security system.

FIG. 8 shows an example of a security system having features of the WSN described with respect to FIGS. 1 to 7 and having the various functionalities described herein. As shown in FIG. 8, correlation processing receives inputs from certain constrained nodes (although these can also be fully functional nodes). These inputs may include credential information and video information, and the correlation processing may produce correlated results that are sent over the network. Context management processing receives inputs from certain constrained nodes (although these can also be fully functional nodes) e.g., credential information and video and grouping information, and performs context processing with results sent over the network. The network supports operation of emergency exit indicators; emergency cameras as well as distributed rule processing and rule engine/messaging processing. Range extenders are used with e.g., gateways, and a real time location system receives inputs from various sensors (e.g., constrained type) as shown. Servers interface to the WSN via a cloud computing configuration and parts of some networks can be run as sub-nets.

The sensors provide in addition to an indication that something is detected in an area within the range of the sensors, detailed additional information that can be used to evaluate what that indication may be without the intrusion detection panel being required to perform extensive analysis of inputs to the particular sensor.

For example, a motion detector could be configured to analyze the heat signature of a warm body moving in a room to determine if the body is that of a human or a pet. Results of that analysis would be a message or data that conveys information about the body detected. Various sensors thus are used to sense sound, motion, vibration, pressure, heat, images, and so forth, in an appropriate combination to detect a true or verified alarm condition at the intrusion detection panel.

Recognition software can be used to discriminate between objects that are a human and objects that are an animal; further facial recognition software can be built into video cameras and used to verify that the perimeter intrusion was the result of a recognized, authorized individual. Such video cameras would comprise a processor and memory and the recognition software to process inputs (captured images) by the camera and produce the metadata to convey information regarding recognition or lack of recognition of an individual captured by the video camera. The processing could also alternatively or in addition include information regarding characteristic of the individual in the area captured/monitored by the video camera. Thus, depending on the circumstances, the information would be either metadata received from enhanced motion detectors and video cameras that performed enhanced analysis on inputs to the sensor that gives characteristics of the perimeter intrusion or a metadata resulting from very complex processing that seeks to establish recognition of the object.

Sensor devices can integrate multiple sensors to generate more complex outputs so that the intrusion detection panel can utilize its processing capabilities to execute algorithms that analyze the environment by building virtual images or signatures of the environment to make an intelligent decision about the validity of a breach.

Memory stores program instructions and data used by the processor of the intrusion detection panel. The memory may be a suitable combination of random access memory and read-only memory, and may host suitable program instructions (e.g. firmware or operating software), and configuration and operating data and may be organized as a file system or otherwise. The stored program instruction may include one or more authentication processes for authenticating one or more users. The program instructions stored in the memory of the panel may further store software components allowing network communications and establishment of connections to the data network. The software components may, for example, include an internet protocol (IP) stack, as well as driver components for the various interfaces, including the interfaces and the keypad. Other software components suitable for establishing a connection and communicating across network will be apparent to those of ordinary skill.

Program instructions stored in the memory, along with configuration data may control overall operation of the panel.

The monitoring server includes one or more processing devices (e.g., microprocessors), a network interface and a memory (all not illustrated). The monitoring server may physically take the form of a rack mounted card and may be in communication with one or more operator terminals (not shown). An example monitoring server is a SURGARD™ SG-System III Virtual, or similar system.

The processor of each monitoring server acts as a controller for each monitoring server, and is in communication with, and controls overall operation, of each server. The processor may include, or be in communication with, the memory that stores processor executable instructions controlling the overall operation of the monitoring server. Suitable software enable each monitoring server to receive alarms and cause appropriate actions to occur. Software may include a suitable Internet protocol (IP) stack and applications/clients.

Each monitoring server of the central monitoring station may be associated with an IP address and port(s) by which it communicates with the control panels and/or the user devices to handle alarm events, etc. The monitoring server address may be static, and thus always identify a particular one of monitoring server to the intrusion detection panels. Alternatively, dynamic addresses could be used, and associated with static domain names, resolved through a domain name service.

The network interface card interfaces with the network to receive incoming signals, and may for example take the form of an Ethernet network interface card (NIC). The servers may be computers, thin-clients, or the like, to which received data representative of an alarm event is passed for handling by human operators. The monitoring station may further include, or have access to, a subscriber database that includes a database under control of a database engine. The database may contain entries corresponding to the various subscriber devices/processes to panels like the panel that are serviced by the monitoring station.

All or part of the processes described herein and their various modifications (hereinafter referred to as "the processes") can be implemented, at least in part, via a computer program product, i.e., a computer program tangibly embodied in one or more tangible, physical hardware storage devices that are computer and/or machine-readable storage devices for execution by, or to control the operation of, data processing apparatus, e.g., a programmable processor, a computer, or multiple computers. A computer program can be written in any form of programming language, including compiled or interpreted languages, and it can be deployed in any form, including as a stand-alone program or as a module, component, subroutine, or other unit suitable for use in a computing environment. A computer program can be deployed to be executed on one computer or on multiple computers at one site or distributed across multiple sites and interconnected by a network.

Actions associated with implementing the processes can be performed by one or more programmable processors executing one or more computer programs to perform the functions of the calibration process. All or part of the processes can be implemented as, special purpose logic circuitry, e.g., an FPGA (field programmable gate array) and/or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only storage area or a random access storage area or both. Elements of a computer (including a server) include one or more processors for executing instructions and one or more storage area devices for storing instructions and data. Generally, a computer will also include, or be operatively coupled to receive data from, or transfer data to, or both, one or more machine-readable storage media, such as mass storage devices for storing data, e.g., magnetic, magneto-optical disks, or optical disks.

Tangible, physical hardware storage devices that are suitable for embodying computer program instructions and data include all forms of non-volatile storage area, including by way of example, semiconductor storage area devices, e.g., EPROM, EEPROM, and flash storage area devices; magnetic disks, e.g., internal hard disks or removable disks; magneto-optical disks; and CD-ROM and DVD-ROM disks and volatile computer memory, e.g., RAM such as static and dynamic RAM, as well as erasable memory, e.g., flash memory.

In addition, the logic flows depicted in the figures do not require the particular order shown, or sequential order, to achieve desirable results. In addition, other actions may be provided, or actions may be eliminated, from the described flows, and other components may be added to, or removed from, the described systems. Likewise, actions depicted in the figures may be performed by different entities or consolidated.

Elements of different embodiments described herein may be combined to form other embodiments not specifically set forth above. Elements may be left out of the processes, computer programs, Web pages, etc. described herein without adversely affecting their operation. Furthermore, various separate elements may be combined into one or more individual elements to perform the functions described herein.

Other implementations not specifically described herein are also within the scope of the following claims.

What is claimed is:

1. A distributed device network comprising a plurality of building network devices each configured to perform a monitoring or control function for a physical state or condition of a building, the building network devices connected to a wireless network configured to connect to a cloud computing system via an external network, the building network devices comprising memory configured to store instructions thereon, that when executed by one or more processors, cause the one or more processors to:
   receive, from a server of the cloud computing system by a first building network device of the plurality of building network devices, an application, the application comprising an information processing function of the cloud computing system, the information processing function comprising an operation performed on data generated by at least one of the plurality of building network devices to generate a result used to perform the control function for the physical state or condition of the building;
   when the wireless network is connected to the cloud computing system, send data to the cloud computing system for execution of the information processing function using the data by the cloud computing system; and
   when the wireless network is disconnected from the cloud computing system, execute, by the first building network device, the application to provide the information processing function of the cloud computing system.

2. The distributed device network of claim 1, the plurality of building network devices comprising a package engine, wherein the application is a packaged application, wherein the package engine manages execution of one or more packaged applications.

3. The distributed device network of claim 2, wherein the one or more packaged applications have no external dependencies.

4. The distributed device network of claim 3, wherein each of the one or more packaged applications is associated with a function of one or more functions of the cloud computing system.

5. The distributed device network of claim 4, wherein each of the one or more functions is a microservice.

6. The distributed device network of claim 5, wherein a first function of the one or more functions is a queue function to store information received from one or more end nodes and send the information to one or more of the plurality of building network devices.

7. The distributed device network of claim 5, wherein a second function of the one or more functions is a processing function to perform one or more tasks on information received from one or more of the plurality of building network devices to produce processing results.

8. The distributed device network of claim 5, wherein a third function of the one or more functions is a database function to store in local memory processing results received from one or more of the plurality of building network devices.

9. An edge computing system, comprising:
   a server of a cloud computing system configured to connect to an external network and having a plurality of packaged applications, the cloud computing system configured to receive data and execute an information processing function using the data; and
   a plurality of building network devices each configured to perform a monitoring or control function for a physical state or condition of a building and to connect to a wireless mesh network, the wireless mesh network connected to the external network, the plurality of building network devices comprising one or more processors and memory connected to the one or more processors, the memory having instructions stored thereon, that when executed by the one or more processors, cause the one or more processors to:
   receive, from the server, a first packaged application of the plurality of packaged applications, the first packaged application associated with the information processing function, the information processing function comprising an operation performed on data generated by at least one of the plurality of building network devices to generate a result used to perform the control function for the physical state or condition of the building;
   when the wireless mesh network is connected to the cloud computing system, send data to the cloud computing system for execution of the information processing function using the data by the cloud computing system; and
   when the wireless mesh network is disconnected from the cloud computing system, execute the first packaged application to provide the information processing function of the cloud computing system using the plurality of building network devices;
   wherein each building network device of the plurality of building network devices is a constrained computing device.

10. The edge computing system of claim 9, the plurality of building network devices comprising a package engine, wherein the package engine manages execution of the plurality of packaged applications.

11. The edge computing system of claim 10, wherein the plurality of packaged applications have no external dependencies.

12. The edge computing system of claim 11, wherein each of the plurality of packaged applications is associated with a function of one or more functions of the cloud computing system.

13. The edge computing system of claim 12, wherein each of the one or more functions is a microservice for the cloud computing system.

14. The edge computing system of claim 13, wherein a first function of the one or more functions is a queue function to store information received from at least one building network device of the plurality of building network devices, or an end node.

15. The edge computing system of claim 13, wherein a second function of the one or more functions is a processing function to perform one or more tasks on information received from at least one building network device of the plurality of building network devices, or an end node, and produce processing results.

16. The edge computing system of claim 13, wherein a third function of the one or more functions is a database function to store processing results received from one or more building network devices of the plurality of building network devices.

17. A system, comprising:
a server of a cloud computing system configured to connect to an external network and having a plurality of packaged applications associated with one or more functions of the cloud computing system, the cloud computing system configured to receive data and execute an information processing function using the data, wherein the plurality of packaged applications are microservices having no external dependencies; and
a plurality of building network devices each configured to perform monitoring or control functions for a physical state or condition of a building and to form a wireless mesh network, the wireless mesh network connected to the external network, the plurality of building network devices comprising a package engine, one or more processors, and memory connected to the one or more processors, the memory having instructions stored thereon, that when executed by the one or more processors, cause the package engine to:
receive, from the server, a first packaged application of the plurality of packaged applications, the first packaged application associated with the information processing function of the cloud computing system, the information processing function comprising an operation performed on data generated by at least one of the plurality of building network devices to generate a result used to perform the control functions for the physical state or condition of the building;
when the wireless mesh network is connected to the cloud computing system, send data to the cloud computing system for execution of the information processing function using the data by the cloud computing system; and
when the wireless mesh network is disconnected from the cloud computing system, execute the first packaged application to provide the information processing function of the cloud computing system using the plurality of building network devices.

18. The system of claim 17, wherein a first function of the one or more functions is a queue function to store information received from a source and send the information to a destination.

19. The system of claim 18, wherein a second function of the one or more functions is a processing function to perform one or more tasks on the information and produce processing results.

20. The system of claim 19, wherein a third function of the one or more functions is a database function to store the processing results.

* * * * *